United States Patent [19]

Ting et al.

[11] Patent Number: 5,688,805

[45] Date of Patent: Nov. 18, 1997

[54] TRICYCLIC DERIVATIVES, COMPOSITIONS AND METHODS OF USE

[75] Inventors: Pauline C. Ting, New Providence; Daniel M. Solomon, Edison; Wing C. Tom, Cedar Grove, all of N.J.; Steven K. White, San Diego, Calif.; James J. Kaminski, Long Valley, N.J.; Shing-Chun C. Wong, Union, N.J.; Nicholas I. Carruthers, North Plainfield, N.J.

[73] Assignee: Schering Corporation, Kenilworth, N.J.

[21] Appl. No.: 458,581

[22] Filed: Jun. 2, 1995

Related U.S. Application Data

[62] Division of Ser. No. 162,748, Dec. 6, 1993, Pat. No. 5,464,840.

[51] Int. Cl.$^6$ .................................................... A61K 31/445
[52] U.S. Cl. .......................... 514/277; 514/290; 514/291; 514/320; 514/325; 514/334; 514/354
[58] Field of Search .................................. 514/290, 291, 514/277, 320, 325, 337, 354; 546/89, 93, 196, 203, 281.7, 285

[56] References Cited

U.S. PATENT DOCUMENTS

| | | |
|---|---|---|
| 2,985,660 | 5/1961 | Judd . |
| 3,357,986 | 12/1967 | Villani ........................................ 546/93 |
| 3,372,196 | 3/1968 | Engelhardt . |
| 3,479,356 | 11/1969 | Fouche . |
| 3,595,865 | 7/1971 | Sorenson et al. . |
| 3,922,305 | 11/1975 | Engelhardt . |
| 3,944,566 | 3/1976 | Winter et al. . |
| 3,978,121 | 8/1976 | Engelhardt . |
| 3,981,917 | 9/1976 | Engelhardt . |
| 4,070,373 | 1/1978 | Winter et al. . |
| 4,626,542 | 12/1986 | King et al. . |
| 4,758,577 | 7/1988 | Young . |
| 4,826,853 | 5/1989 | Piwinski et al. . |
| 4,863,931 | 9/1989 | Schumacher . |
| 4,996,321 | 2/1991 | Baldwin et al. . |
| 5,089,496 | 2/1992 | Piwinski et al. . |
| 5,104,876 | 4/1992 | Piwinski et al. . |
| 5,151,423 | 9/1992 | Piwinski et al. . |
| 5,430,032 | 7/1995 | Wong . |
| 5,438,062 | 8/1995 | Piwinski . |

FOREIGN PATENT DOCUMENTS

| | | |
|---|---|---|
| 0341860 | 4/1989 | European Pat. Off. . |
| 0 515 158 A1 | 11/1992 | European Pat. Off. . |
| 1274262 | 5/1972 | United Kingdom . |
| 88/03138 | 5/1988 | WIPO . |
| 89/10363 | 11/1989 | WIPO . |
| 89/10369 | 11/1989 | WIPO . |
| WO92/11034 | 7/1992 | WIPO . |

OTHER PUBLICATIONS

Chem. Abstracts Reg. No. 55286–80–1.
Chem. Abstracts Reg. No. 23509–37–7.
Chem. Abstracts Reg. No. 23485–60–1.
Chem. Abstracts Reg. No. 138729–88–1.
Chem. Abstracts Reg. No. 138707–21–8.
Chem. Abstracts Reg. No. 37028–07–2.

*Primary Examiner*—C. Warren Ivy
*Assistant Examiner*—Garth M. Dahlen
*Attorney, Agent, or Firm*—James M. Gould

[57] ABSTRACT

Disclosed are compounds of Formula I:

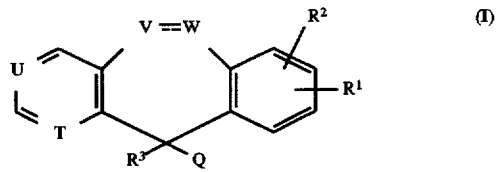

or a pharmaceutically acceptable salt or solvate thereof. Also disclosed are pharmaceutical compositions containing compounds of Formula I, methods for inhibiting tumor necrosis factor-α and methods for treating septic shock, inflammation, or allergic disease.

19 Claims, No Drawings

TRICYCLIC DERIVATIVES, COMPOSITIONS AND METHODS OF USE

The present application is a division of U.S. application Ser. No. 08/162,748, filed Dec. 6, 1993, now U.S. Pat. No. 5,464,840 the benefit of which is claimed pursuant to the provisions of 35 U.S.C. §120.

FIELD OF THE INVENTION

The present invention relates to tricyclic derivatives, pharmaceutical compositions and methods of using such derivatives. The compounds of the present invention inhibit tumor necrosis factor α ("TNF-α").

BACKGROUND OF THE INVENTION

Tumor necrosis factor α ("TNF-α") is a polypeptide cytokine known to induce a variety of inflammatory and metabolic processes in vivo. See, e.g., *Ann. Rev. Immunol.* 7:625 (1989). However, overproduction or inappropriate production of TNF-α has been shown to be involved in several pathological conditions, including septic shock and various allergic diseases and inflammatory conditions. See, e.g., *Immunol Res.* 10:122 (1991), *Science* 229:869 (1985) and *Proc. Natl. Acad. Sci.* 89:7375 (1992). Thus, compounds that could inhibit TNF-α would be quite valuable in treating these conditions.

In view of the substantial interest in agents that inhibit TNF-α, the identification of compounds having anti-TNF-α activity would be a valuable contribution to the art. This invention provides just such a contribution by providing novel compounds having anti-TNF-α activity. In addition, this invention provides methods of using such compounds.

SUMMARY OF THE INVENTION

We have now unexpectedly found that compounds having the general formula I (set forth below) provide surprisingly good activity as inhibitors of tumor necrosis factor α (TNF-α). More specifically, we believe that the compounds of formula I provide this activity by inhibiting the biosynthesis of TNF-α. In view of this surprising anti-TNF-α activity, it is believed that compounds of formula I are useful in the relief of septic shock, allergic diseases, and inflammatory conditions.

Formula I is as follows:

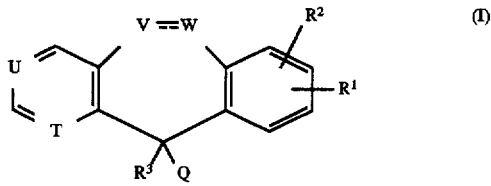

or a pharmaceutically acceptable salt or solvate thereof, wherein:

one of T and U represents N and the other represents =CH—; or each of T and U represents =CH—;

the ——— line represents an optional double bond; when ——— is a double bond, each of V and W represents =CH—; when ——— represents a single bond, one of V and W represents oxygen and the other represents —CH$_2$—; or each of V and W represents —CH$_2$—;

$R^1$ and $R^2$ are each independently selected from the group consisting of H and halogen;

$R^3$ is H; alkyl; alkenyl; alkynyl; aryl; alkaryl; aralkyl; cycloalkyl; alkoxy; $(CH_2)_nOR^{10}$; $(CH_2)_nCOOR^{10}$, wherein n is 1 to 3 and $R^{10}$ is H or lower alkyl; or $S(O)_eR^{11}$, wherein e is 0 or 2 and $R^{11}$ is alkyl or aryl;

Q represents

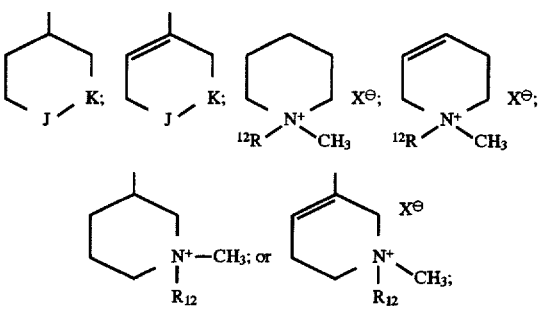

wherein one of J and K represents

and the other represents —CH$_2$—, with the proviso that when $R^3$ is H, Q is limited to either:

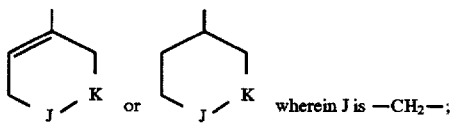 wherein J is —CH$_2$—;

$R^{12}$ is lower alkyl;

$R^{16}$ is H; lower alkyl; aryl; aralkyl; alkaryl; $COR^{17}$ or $C(O)OR^{18}$, wherein $R^{17}$ is H or lower alkyl or aryl, $R^{18}$ is lower alkyl or aryl; and X represents halogen.

More preferred compounds include those of Formula I wherein $R^3$ is alkyl. When $R^3$ is alkyl, $R^3$ is preferably an alkyl group other than —CH$_3$, more preferably an alkyl group having from two to six carbon atoms, and more preferably still, $R^3$ is propyl.

More preferred compounds also include those of Formula I wherein $R^3$ is alkenyl, and more preferably wherein $R^3$ is allyl.

More preferred compounds also include those of Formula I wherein each of T and U represents =CH—.

Furthermore, preferred compounds also include those of Formula I wherein Q is:

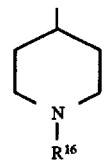

or
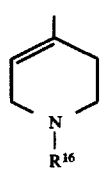
wherein $R^{16}$ is H, lower alkyl, aryl, aralkyl or alkaryl.
Representative compounds of this invention include, but are not limited to:
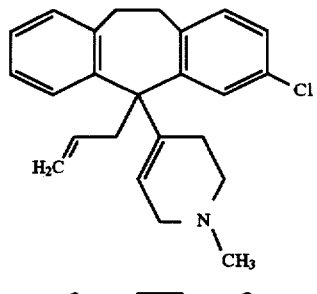
(IA)
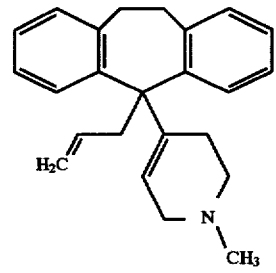
(IB)
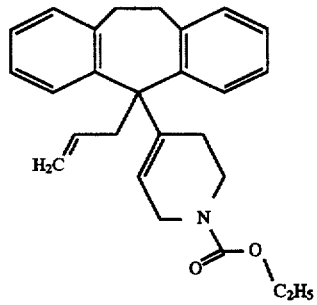
(IC)
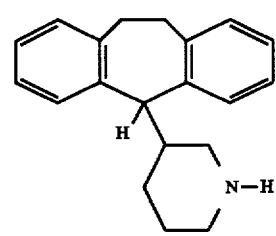
(ID)
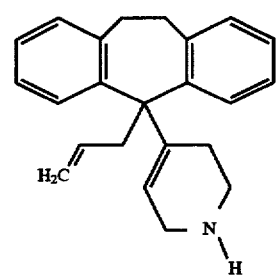
(IE)
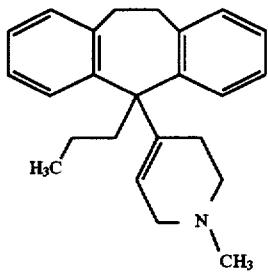
(IF)
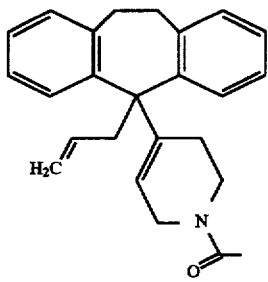
(IG)
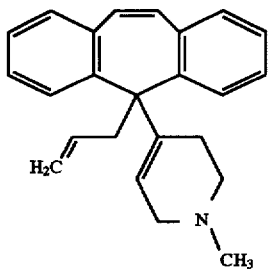
(IH)
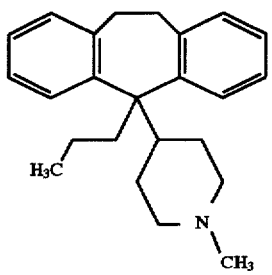
(IJ)
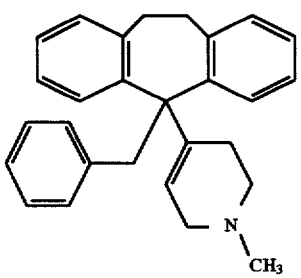
(IK)
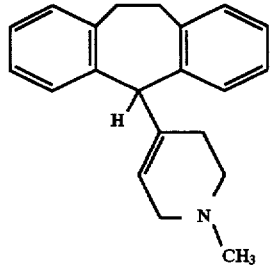
(IL)

-continued
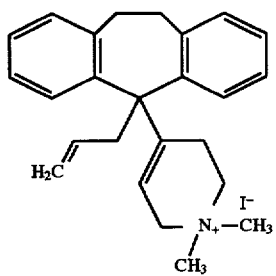
(IM)
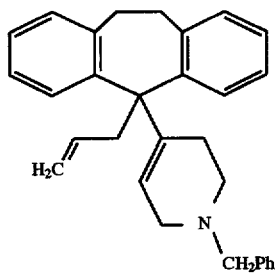
(IN)
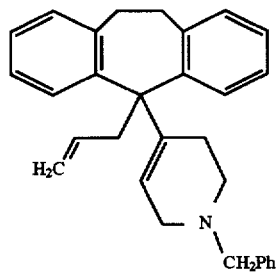
(IO)
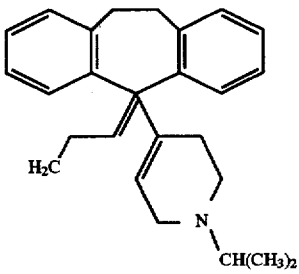
(IP)
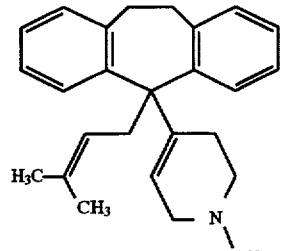
(IQ)
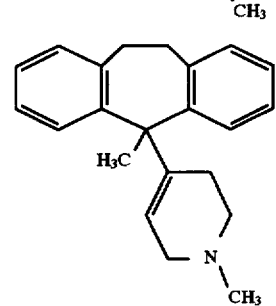
(IR)
-continued
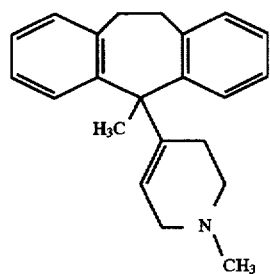
(IS)
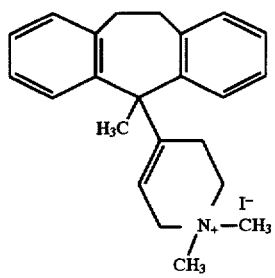
(IT)
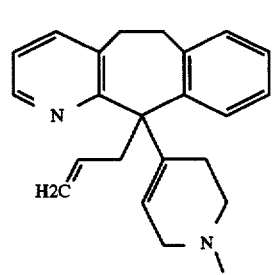
(IX)
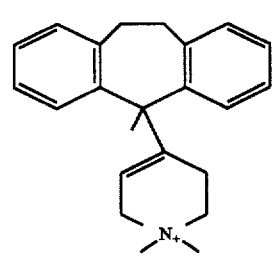
(IY)
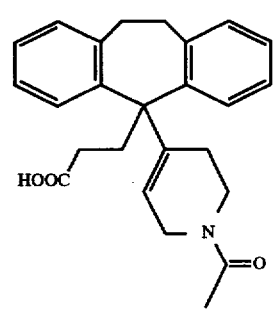
(IZ)

-continued

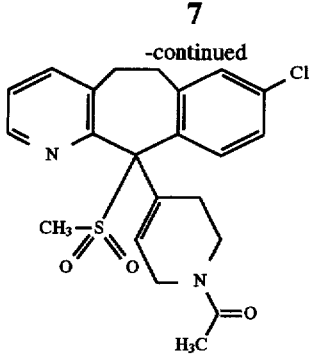
(IAA)

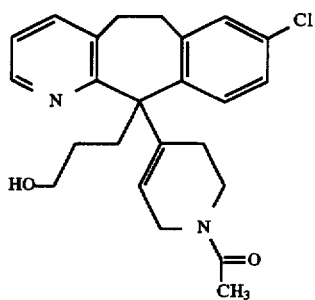
(IBB)

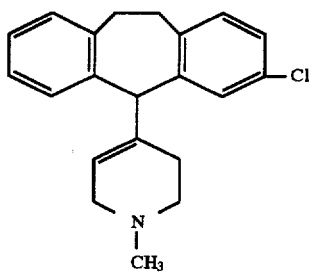
(ICC)

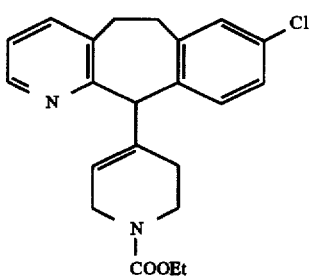
(IDD)

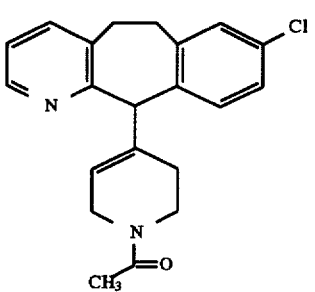
(IEE)

This invention also provides a pharmaceutical composition comprising an effective amount of a compound of Formula I in combination with a pharmaceutically acceptable carrier.

In addition, this invention provides a method for inhibiting TNF-α in a mammal comprising administering to the mammal an amount of a compound of Formula I effective to inhibit TNF-α.

In view of the surprising anti-TNF-α activity of compounds of formula I, this invention provides the following methods of treatment:

a method for treating inflammation in a mammal comprising administering to the mammal an effective anti-inflammatory amount of a compound of Formula I;

a method for treating septic shock in a mammal comprising administering to the mammal an effective anti-septic shock amount of a compound of Formula I; and a method for treating allergic reaction in a mammal comprising administering to the mammal an effective anti-allergic amount of a compound of Formula I.

It also has been surprisingly found that the following known compound (hereafter referred to as Compound K) has anti-TNF-α activity:

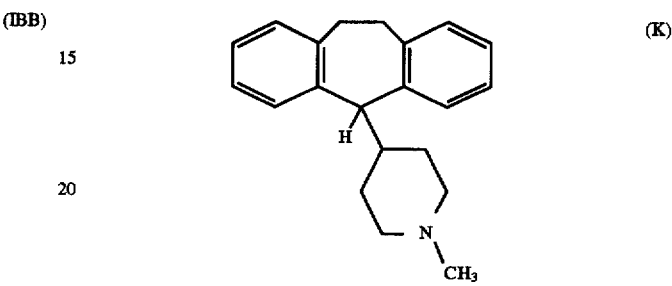
(K)

Heretofore, Compound K was only disclosed as having cardiovascular activity. (See King et al, U.S. Pat. No. 4,626,542).

Accordingly, the present invention also provides a method for inhibiting TNF-α in a mammal comprising administering to the mammal an amount of Compound K effective to inhibit TNF-α.

In view of the surprising anti-TNF activity of Compound K, this invention also provides the following methods of treatment:

a method for treating inflammation in a mammal comprising administering to the mammal an effective anti-inflammatory amount of Compound K;

a method for treating septic shock in a mammal comprising administering to the mammal an effective anti-septic shock amount of Compound K; and a method for treating allergic reaction in a mammal comprising administering to the mammal an effective anti-allergic amount of Compound K.

The present invention will be described in detail below in connection with several preferred embodiments. However, additional embodiments of the present invention will be apparent to those having ordinary skill in the art.

DETAILED DESCRIPTION OF THE INVENTION

As used herein, the following terms are used as defined below unless otherwise indicated:

alkyl—(including the alkyl portions of alkoxy and cycloalkyl)—represents straight and branched carbon chains and contains from one to twenty carbon atoms, preferably one to six carbon atoms;

alkenyl—(including the alkenyl portions of cycloalkenyl) represents straight and branched carbon chains having at least one carbon to carbon double bond and containing from 2 to 12 carbon atoms, preferably from 2 to 6 carbon atoms;

alkynyl—represents straight and branched carbon chains having at least one carbon to carbon triple bond and containing from 2 to 12 carbon atoms, preferably from 2 to 6 carbon atoms;

aryl—represents a carbocyclic group (preferably phenyl or substituted phenyl) containing from 6 to 14 carbon atoms and having at least one phenyl or fused phenylene ring, with all available substitutable carbon atoms of the carbocyclic group being intended as possible points of attachment, said carbocyclic group being optionally substituted with one or more of halo, alkyl, hydroxy, alkoxy, phenoxy, cyano, cycloalkyl, alkenyloxy, alkynyloxy, —SH, —S(O)$_e$R$^{12}$ (wherein e is 1 or 2 and R$^{12}$ is alkyl or aryl), —CF$_3$, amino, alkylamino, dialkylamino, —COOR$^{12}$ or —NO$_2$;

acyl—(including the acyl portions of acyloxy) represents —C(O)-alkyl, —C(O)-alkenyl, —C(O)-alkynyl, —C(O)-cycloalkyl, —C(O)-cycloalkenyl or —C(O)-cycloalkynyl;

alkaryl—represents an aryl group, as defined above, in which an alkyl group, as defined above, is substituted for one of the aryl H atoms;

alkoxy—represents an alkyl group, as defined above, attached to a molecule through an oxygen molecule (—O-alkyl);

alkoxymethyl—represents an alkoxy group as defined above attached to a molecule through a methylene group;

aralkyl—represents an alkyl group, as defined above, in which an aryl group, as defined above, is substituted for one of the alkyl H atoms;

and halo—represents fluoro, chloro, bromo and iodo.

Certain compounds of the invention may exist in different isomeric (e.g., enantiomers and diastereoisomers) as well as conformational forms. The invention contemplates all such isomers both in pure form and in admixture, including racemic mixtures. Tautomeric forms are also included.

The compounds of Formula I can exist in unsolvated as well as solvated forms, including hydrated forms, e.g., hemi-hydrate. In general, the solvated forms, with pharmaceutically acceptable solvents such as water, ethanol and the like are equivalent to the unsolvated forms for purposes of the invention.

Lines drawn into the ring systems indicate that the indicated bond may be attached to any of the substitutable ring carbon atoms.

Certain compounds of the invention will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds of the invention also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

The invention disclosed herein is exemplified by the following preparative examples, which should not be construed to limit the scope of the disclosure. Alternative synthetic pathways and analogous structures within the scope of the invention may be apparent to those of ordinary skill in the art. Further, those skilled in the art will recognize that the reactions are conducted under conditions, e.g., temperature, that will allow the reaction to proceed at a reasonable rate to completion. Unless indicated otherwise, the substituents for the formulas given hereinafter have the same definition as those of Formula I.

PREPARATIVE METHODS AND REACTION SCHEMES

Scheme 1:

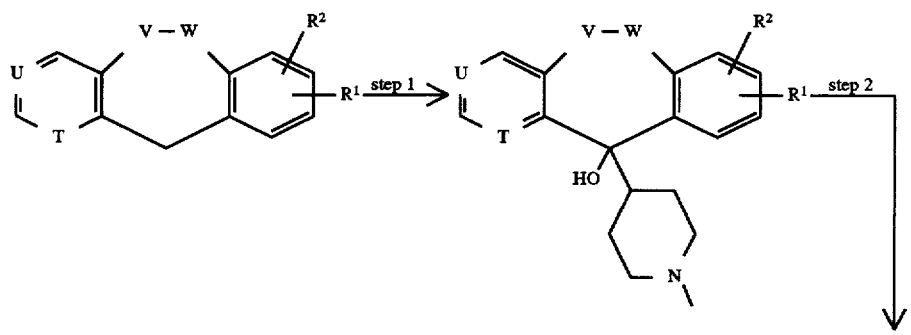

-continued
Scheme 1:

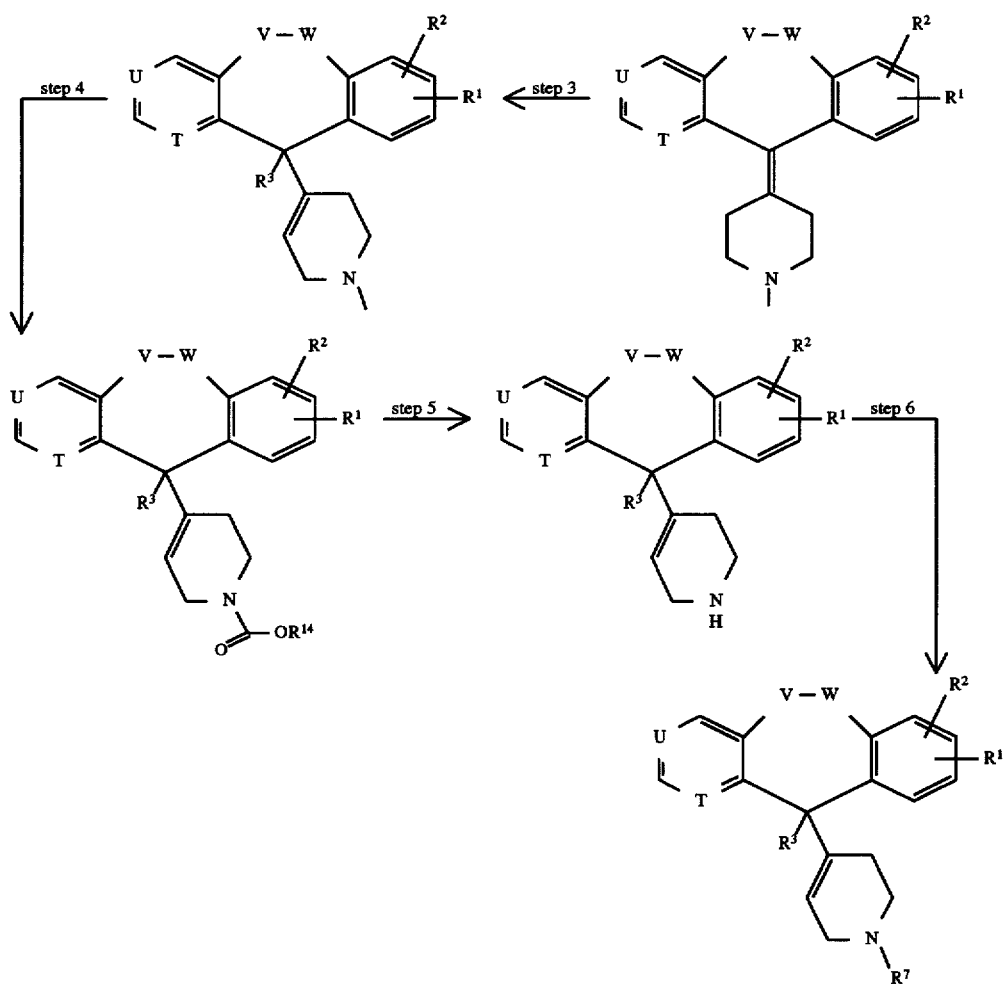

Step 1: This step is preferably carried out by adding the grignard reagent of 4-chloro-N-methyl-piperidine in an inert solvent such as ether (e.g. diethyl ether, tetrahydrofuran, or dioxane) under an inert atmosphere (nitrogen or argon). Preferred temperatures range between 0° C. and 60° C.

Step 2: This step is preferably carried out with strong acid (e.g. hydrochloric acid, sulfuric acid, or triflic acid) in water at temperatures between 25° C. and 100° C.

Step 3: This step is preferably carried out by first adding a strong base (e.g. n-butyl lithium, sec-butyl lithium, or lithium diisopropylamide) in an inert solvent such as ether (e.g. diethyl ether, tetrahydrofuran, or dioxane) under an inert atmosphere (nitrogen or argon) at temperatures between −78° C. and 0° C. Subsequently, the alkylating agent $R^3L$ is added wherein L represents a good leaving group, e.g. L can be chloride, bromide, iodide, mesylate, or tosylate.

Step 4: This step is preferably carried out with a suitable chloroformate reagent $R^{14}OCOCl$ and a mild base (e.g. pyridine or potassium carbonate) in an inert solvent (e.g. benzene, toluene, or acetonitrile). Preferred temperature range is between 25° C. and 110° C.

Step 5: This step is preferably carried out under basic (e.g. sodium hydroxide, potassium hydroxide, or barium hydroxide in water with ethylene glycol, methanol, ethanol, tetrahydrofuran, dioxane, or diglyme) or acidic (e.g. hydrochloric acid, hydrobromic acid, or zinc in acetic acid or water with tetrahydrofuran, dioxane, or diglyme) conditions. Any suitable temperature can be used with preferable temperatures between 25° C. and 100° C.

Step 6: This step is preferably carried out by first adding an amine base (e.g. pyridine, collidine, or triethylamine) in an inert solvent such as chlorinated hydrocarbons (e.g. dichloromethane, 1,2-dichloroethane, or chloroform) or a strong base (n-butyl lithium, sodium hydride, potassium hydride, lithium diisopropyl amide, or potassium bis (trimethylsilyl)amide) in an inert solvent such as ether (e.g. diethyl ether, tetrahydrofuran, or dioxane) or polar aprotic solvent (e.g. N,N-dimethylformamide or N,N-dimethylacetamide) to the tricyclic amine under an inert atmosphere (nitrogen or argon). Subsequently, the alkylating or acylating agent $R^7L$ is added wherein L represents a good leaving group, e.g. L can be chloride, bromide, iodide, mesylate, or tosylate. Any suitable temperature can be used between −78° C. and 80° C.

Scheme 2

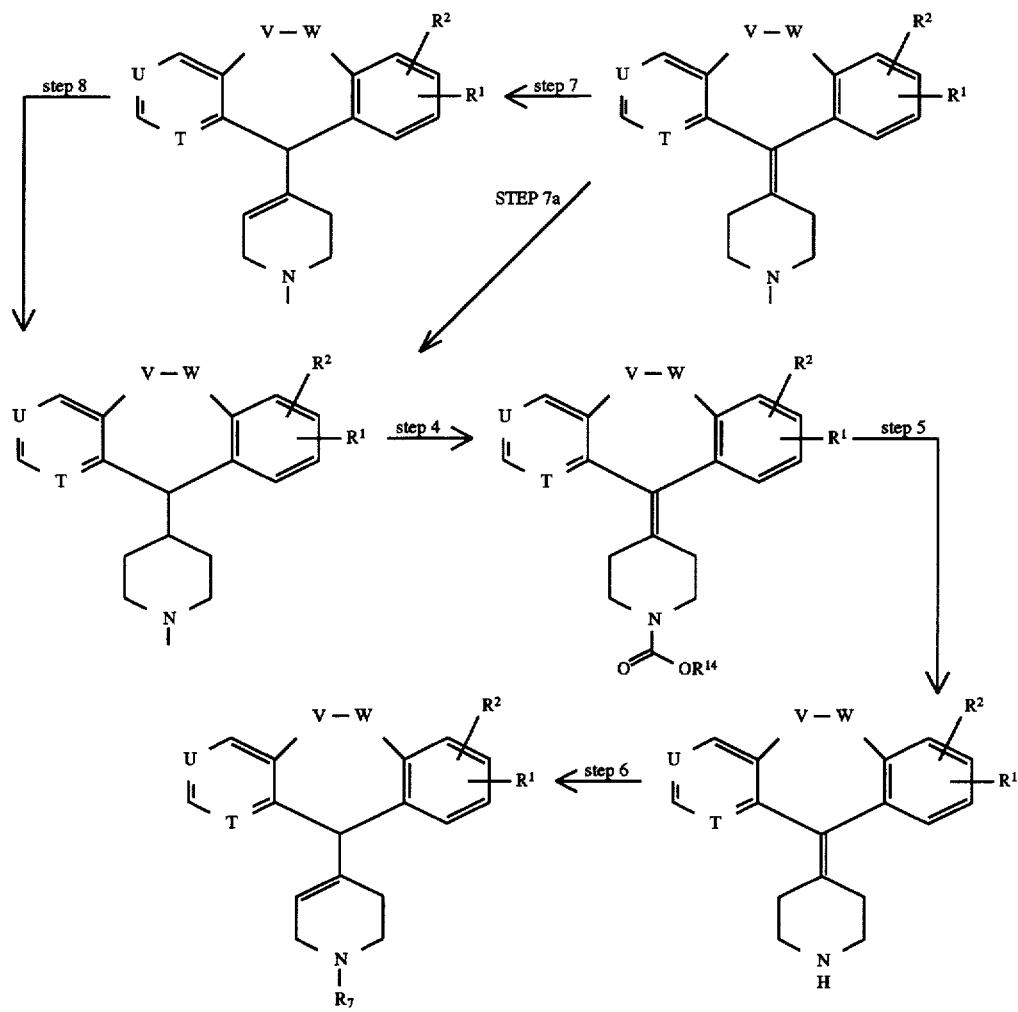

Step 7: This step is preferably carried out by first adding a strong base (e.g. n-butyl lithium, sec-butyl lithium, or lithium diisopropylamide) in an inert solvent such as ether (e.g. diethyl ether, tetrahydrofuran, or dioxane) under an inert atmosphere (nitrogen or argon) at temperatures between −78° C. and 0° C. Subsequently, a proton source (e.g. methanol, ethanol or acetic acid) is added.

Step 8: This step is preferably carried out by hydrogenation with a catalyst (e.g. palladium on carbon or platinum oxide) in an inert solvent (e.g. methanol, ethanol, ethyl acetate, or acetic acid) at 25° C.

Step 4: This step is described above for Scheme 1.

Step 5: This step is described above for Scheme 1.

Step 6: This step is described above for Scheme 1.

Step 7a: This step applies where U or T in formula I is Nitrogen and is preferably carried out by adding a strong reducing agent such as lithium aluminum hydride in an inert solvent such as tetrahydrofuran at a temperature of from 25° to 75° C.

Scheme 3

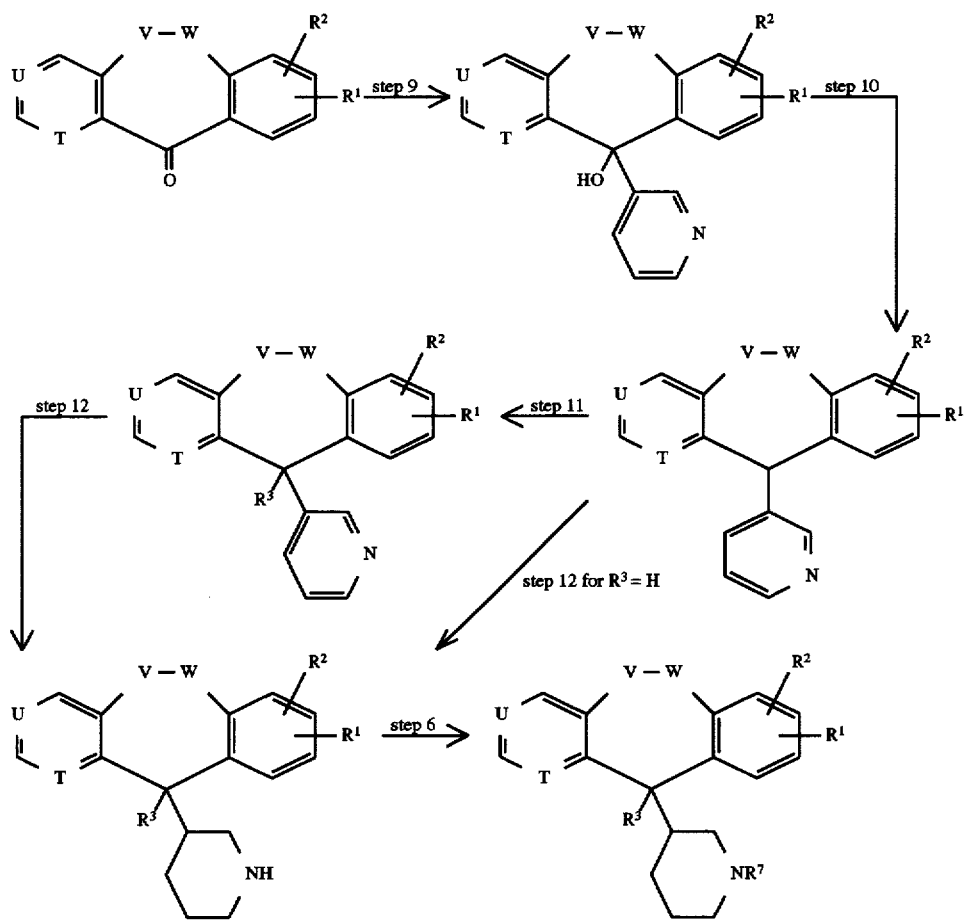

Step 9: This step is preferably carried out by adding the lithium reagent of 3-chloropyridine in an inert solvent such as ether (e.g. diethyl ether, tetrahydrofuran, or dioxane) under an inert atmosphere (nitrogen or argon). Preferred temperature range is between −78° C. and 25° C.

Step 10: This step is preferably carried out with hydroiodic acid and hydrochloric acid in acetic acid at temperatures between 100° C. to 130° C. Alternatively, the alcohol moiety can be converted into a good leaving group L (e.g. chloride, bromide, mesylate, or tosylate) which can be removed by a suitable reducing agent.

Step 11: This step is preferably carried out by first adding a strong base (e.g. n-butyl lithium, sec-butyl lithium, sodium amide, potassium amide, potassium bis(trimethylsilyl)amide, or lithium diisopropylamide) in an inert solvent such as ether (e.g. diethyl ether, tetrahydrofuran, or dioxane) or ammonia under an inert atmosphere (nitrogen or argon) at temperatures between −78° C. and 0° C. Subsequently, the alkylating agent $R^3L$ is added wherein L represents a good leaving group, e.g. L can be chloride, bromide, iodide, mesylate, or tosylate.

Step 12: This step is preferably carried out by reduction with sodium in ethanol or hydrogenation with a catalyst (e.g. palladium on carbon, platinum oxide, or rhodium on carbon) in an acidic solvent (e.g. acetic acid, trifluoroacetic acid, or methanol or ethanol with hydrochloric acid) at 25° C.

Step 6: This step is described above for Scheme 1.

GENERAL PROCESSES

Preparation of a compound of formula I

A.

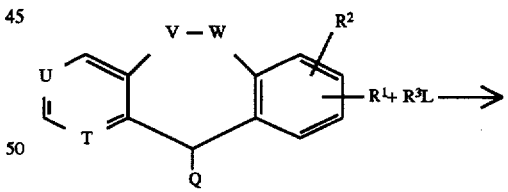

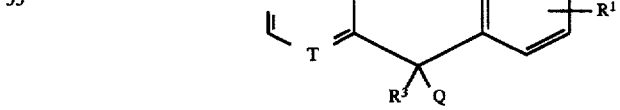

The process is preferably carried out by first adding a strong base (e.g. n-butyl lithium, sec-butyl lithium, sodium amide, potassium amide, lithium diisopropylamide, or potassium bis(trimethylsilyl)amide) to the tricyclic compound in an inert solvent (e.g. ether such as diethyl ether, tetrahydrofuran, or dioxane, or polar solvent such as ammonia, N,N-dimethylformamide, or N,N- dimethylacetamide) under an inert atmosphere (nitrogen or argon). Subsequently, the alkylating agent is added wherein L represents a good leaving group, e.g. L can be chloride, bromide, iodide, mesylate, or tosylate. Any suitable temperature can be used with preferable temperatures between −78° C. and 25° C.

B.

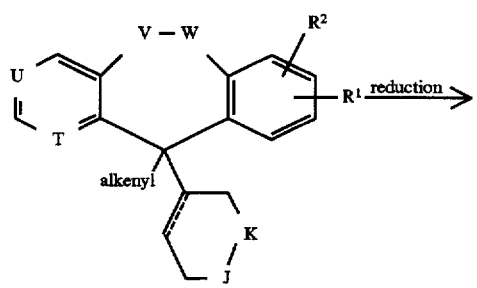

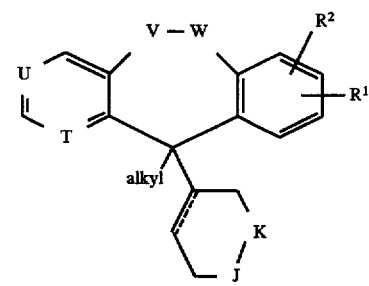

The process is preferably carried out by treating the tricyclic alkene with a catalyst (e.g. palladium on carbon or raney nickel) under a hydrogen atmosphere in an inert solvent (e.g. methanol, ethanol,or ethyl acetate) at ambient temperature.

C.

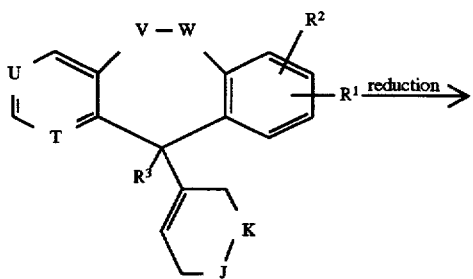

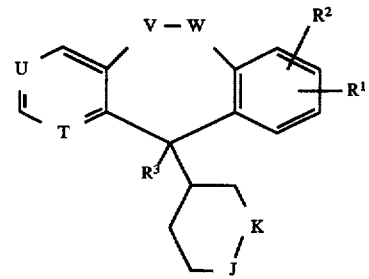

The process is preferably carried out by treating the tricyclic alkene with a catalyst (e.g. palladium on carbon or platinum oxide) under a hydrogen atmosphere in an inert solvent (e.g. methanol, ethanol, ethyl acetate, or acetic acid) at ambient temperature.

D.

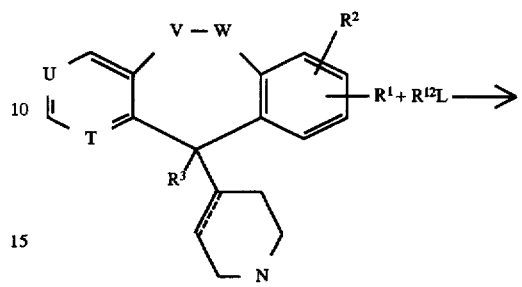

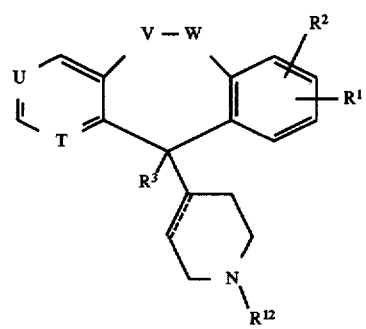

The process is preferably carried out by first adding an amine base (e.g. pyridine, collidine, or triethylamine) in an inert solvent such as chlorinated hydrocarbons (e.g. dichloromethane, 1,2-dichloroethane, or chloroform) or a strong base (n-butyl lithium, sodium hydride, potassium hydride, lithium diisopropyl amide, or potassium bis (trimethylsilyl)amide) in an inert solvent such as ether (e.g. diethyl ether, tetrahydrofuran, or dioxane) or polar aprotic solvent (e.g. N,N-dimethylformamide or N,N-dimethylacetamide) to the tricyclic amine under an inert atmosphere (nitrogen or argon). Subsequently, the alkylating or acylating agent $R^8L$ is added wherein L represents a good leaving group, e.g. L can be chloride, bromide, iodide, mesylate, or tosylate. Any suitable temperature can be used between −78° C. and 80° C.

D.

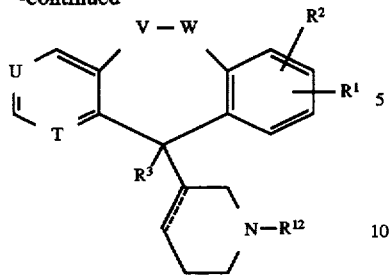

The process is the same as the one described for process D.

F.

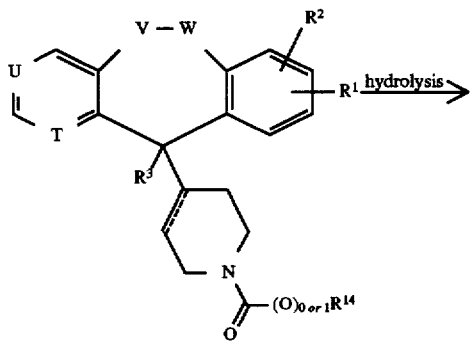

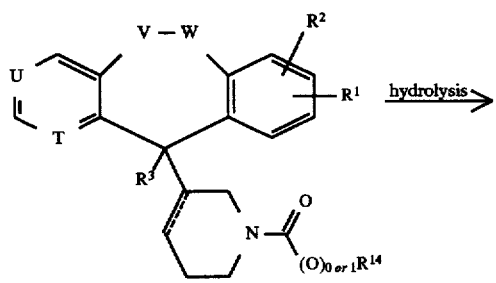

The process is preferably carried out by treating the amide or carbamate compound under basic (e.g. sodium hydroxide, potassium hydroxide, or sodium peroxide in water with ethylene glycol, methanol, ethanol, tetrahydrofuran, dioxane, or diglyme) or acidic (e.g. hydrochloric acid, sulfuric acid, or tosic acid in water with tetrahydrofuran, dioxane, or diglyme) conditions. Any suitable temperature can be used with preferable temperatures between 60° C. and 150° C.

G.

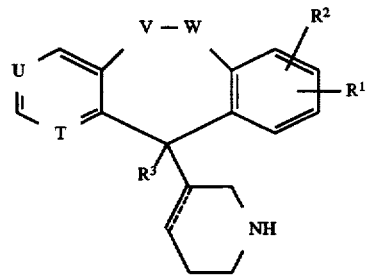

The process is the same as the one described for process F.

H.

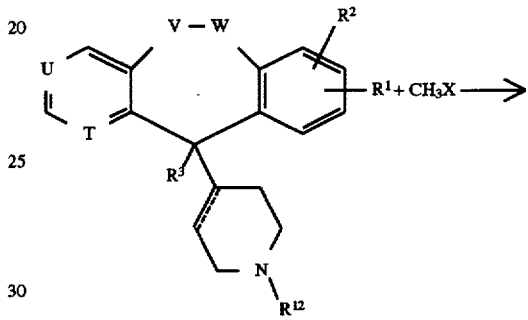

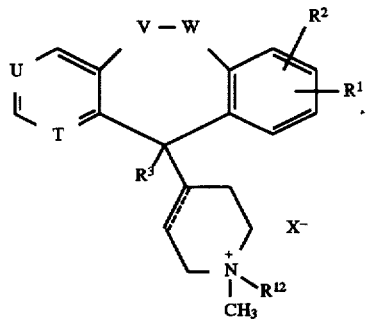

The process is carried out by treating the tricyclic amine with a methylating agent CH$_3$X wherein X represents the counter anion (e.g. X can be chloride, bromide, iodide, sulfate, or tosylate) in an inert solvent such as a protic solvent (e.g. methanol, ethanol, isopropanol, or butanol). Any suitable temperature can be used with preferable temperatures between 25° C. and 100° C.

I.

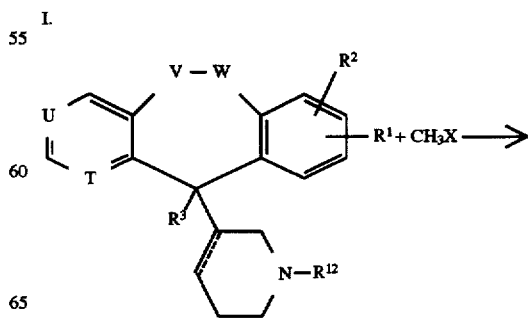

-continued

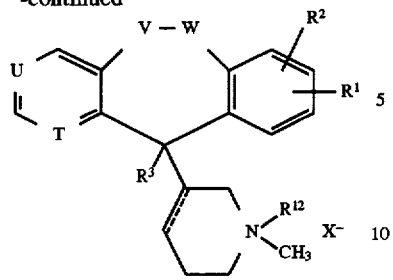

The process is the same as the one described for process H.

SPECIFIC PREPARATIVE EXAMPLES

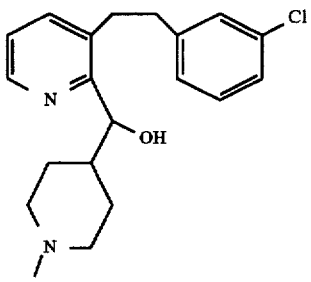

To synthesize an intermediate:

Dissolved [3-(3-chlorophenylethyl)-pyridin-2-yl]-(N-methyl-piperidin-2-yl) ketone (50.0 g, 0.145 mol) in 580 mL of dry methanol under a nitrogen atmosphere, and added sodium borohydride (14.09 g, 0.370 mol) portionwise. Stirred at room temperature for 48 hours. Reduced volume, and poured onto ice. Extracted with dichloromethane. Washed combined organic extracts with saturated NaCl, dried with $Na_2SO_4$, filtered, and evaporated. Purified crude product by flash chromatography on silica gel eluting with 90:9:0.25 then 80:18:0.25 then 75:24:0.5 $CH_2Cl_2$:MeOH:$NH_4OH$. Combined appropriate fractions, and evaporated to give 41.61 g (56% yield) of α-[3-(3-chlorophenylethyl)-pyridin- 2-yl]-4-(N-methyl)-piperidine methanol as an oil.

mass spectrum: (EI) m/e 344 (M+)

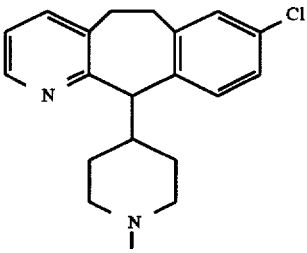

To synthesize an intermediate:

Heated α-[3-(3-chlorophenylethyl)-pyridin-2-yl]-4-(N-methyl)-piperidine methanol (2.0 g, 5.8 mmol) in polyphosphoric acid (80 g) at 170° C. for 37 hours under a nitrogen atmosphere. Cooled reaction mixture to 100° C., and poured onto ice. Carefully added 50 weight % NaOH to pH=10–11. Extracted with ether. Washed combined organic extracts with water and then saturated NaCl, dried with $MgSO_4$, filtered, and evaporated. Purified crude product by flash chromatography on silica gel eluting with 90:9:0.25 $CH_2Cl_2$:MeOH:$NH_4OH$. Combined appropriate fractions, and evaporated to give 0.56 g (29% yield) of 4-[8-chloro-5,6-dihydro-11H-benzo[5,6]cyclohepta[1,2-b]pyridin-11-yl]-1-methyl-1,2,5,6-tetrahydropyridine as an oil. Crystallized product from acetonitrile.

mp=131.5°–133° C.

mass spectrum: (EI) m/e 326 (M+)

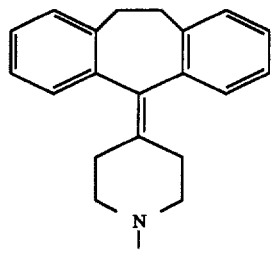

To synthesize an intermediate:

Dissolved cyproheptadine (22.2 g, 0.077 mol) in 150 mL of glacial acetic acid and 20 mL of ethanol. Added platinum oxide catalyst (1.0 g), and hydrogenated on Paar shaker at 57 psi of hydrogen pressure for 5 hours. Filtered, and evaporated filtrate to give a solid. Recrystallized crude product from ether-pet ether to give 21.0 g (94% yield) of 4-(10,11-dihydro-5H-dibenzo[a,d]cyclohepten-5-ylidene)-1-methylpiperidine as a white solid.

mp=108°–110° C.

mass spectrum: (Cl, $CH_4$) m/e 290 (M+1)

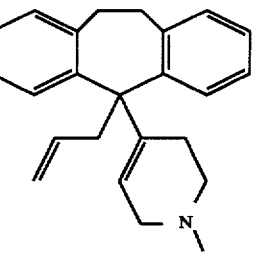

IB

For Compound IB:

Dissolved 4-(10,11-dihydro-5H-dibenzo[a,d]cyclohepten-5-ylidene)-1-methylpiperidine (10 g, 34.6 mmol) in 200 mL of dry THF, and cooled to −78° C. under a nitrogen atmosphere. Added n-butyl lithium (15.2 mL of 2.5M in hexane, 38.0 mmol) dropwise via syringe. Warmed to 0° C., and stirred for 60 mins. Recooled to −78° C., and added allyl bromide (4.6 g, 3.3 mL, 38.0 mmol) dropwise via syringe. Warmed to room temperature slowly, and stirred for 5 hours. Added saturated $NH_4Cl$, and extracted with ether. Dried the combined organic extracts with $MgSO_4$, filtered, and evaporated. Purified the crude product by flash chromatography on silica gel eluting with 5:95:0.1 MeOH:EtOAc:$NH_4OH$. Combined appropriate fractions, and evaporated to give 8.0 g (70% yield) of 4-[10,11-dihydro-5-(2-propenyl)-5H-dibenzo[a,d]cyclohepten-5-yl]-1-methyl-1,2,5,6-tetrahydropyridine as an oil. Dissolved free base in ether, and added 19 weight % HCl-EtOH until acidic. Added additional ether, and let stand to precipitate hydrochloride salt. Recrystallized salt from acetonitrile-ether.

mp=180°–181° C.

mass spectrum: (Cl, CH$_4$) m/e 330 (M+1)

The following compounds were obtained according to a similar manner:

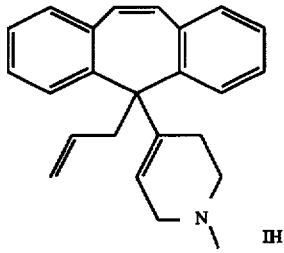
IH mp = 205–215° C.
MS (Cl, CH$_4$) m/e 328 (M + 1)

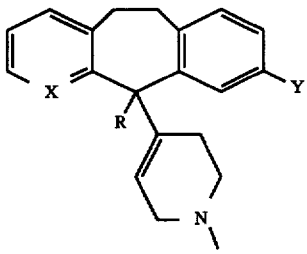

| X | Y | R | salt | mp | Mass Spectrum |
|---|---|---|---|---|---|
| C | H | methyl | maleate | 112–114° C. | (FAB) m/e 304 (M + 1) |
| C | H | prenyl | maleate | 171–172° C. | (Cl, CH$_4$) m/e 358 (M + 1) |
| C | H | benzyl | HCl | 241–245° C. | (Cl, CH$_4$) m/e 380 (M + 1) |
| C | Cl | allyl | maleate | 108–110° C. | (FAB) m/e 364 (M + 1) |
| N | H | allyl | 2 HCl | 200–210° C. | (FAB) m/e 331 (M + 1) |
| N | Cl | benzyl | | 148–152° C. | (FAB) m/e 415 (M + 1) |
| N | Cl | SPh | | foam | (FAB) m/e 433 (M + 1) |
| N | Cl | SMe | | 124–126° C. | (FAB) m/e 371 (M + 1) |
| N | Cl | SEt | | 86–90° C. | (EI) m/e 323 (M−SEt) |

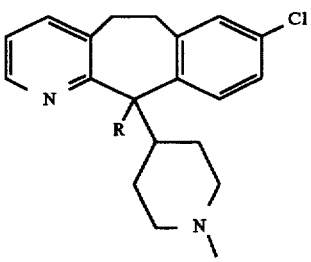

| R | mp | Mass Spectrum |
|---|---|---|
| methyl | | (Cl, CH$_4$) m/e 341 (M + 1) |
| ethyl | | (Cl, CH$_4$) m/e 355 (M + 1) |
| allyl | 148–150° C. | (Cl, CH$_4$) m/e 367 (M + 1) |
| benzyl | | (Cl, CH$_4$) m/e 417 (M + 1) |
| SPh | foam | (FAB) m/e 435 (M + 1) |

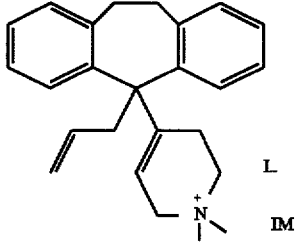
IM

For Compound IM:

Dissolved 4-[10,11-dihydro-5-(2-propenyl)-5H-dibenzo[a,d]cyclohepten-5-yl]-1-methyl-1,2,5,6-tetrahydropyridine (0.50 g, 1.5 mmol) in 30 mL of absolute ethanol, and added 1 mL of iodomethane. Refluxed for 1 hour. Cooled to room temperature, and evaporated to a solid. Triturated with ether, and then recrystallized from dichloromethane-ether to give 0.47 g (66% yield) of 4-[10,11-dihydro-5-(2-propenyl)-5H-dibenzo[a,d]cyclohepten-5-yl]-1,1-dimethyl-1,2,5,6-tetrahydropyridinium iodide as a yellow solid.

mp=150°–160° C.

mass spectrum: (FAB) m/e 344 (M−iodide)

The following compound was obtained according to a similar manner:

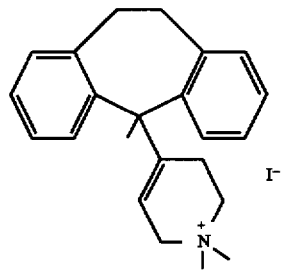
IT mp = 150–160° C.
MS(FAB) m/e 318 (M-iodide)

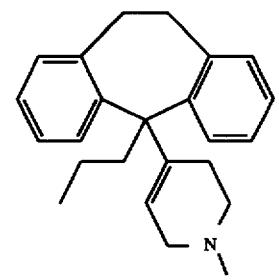
IF

For Compound IF:

Dissolved 4-[10,11-dihydro-5-(2-propenyl)-5H-dibenzo[a,d]cyclohepten-5-yl]-1-methyl-1,2,5,6-tetrahydropyridine (0.39 g, 1.2 mmol) in 50 mL of absolute ethanol, and added a teaspoon of Raney nickel paste. Hydrogenated on a Paar shaker at 17 psi of hydrogen pressure for 16 hours. Filtered to remove catalyst, and evaporated filtrate to a solid. Recrystallized crude product from hexane to give 0.20 g (50% yield) of 4-[10,11-dihydro-5-propyl-5H-dibenzo[a,d]cyclohepten-5-yl]-1-methyl-1,2,5,6-tetrahydropyridine as a white solid.

mp=122°–124° C.

mass spectrum: (Cl, CH₄) m/e 332 (M+1)

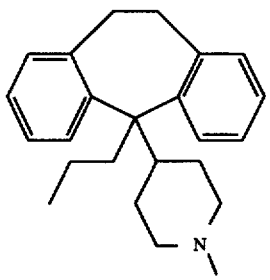

For Compound IJ:

Dissolved 4-[10,11-dihydro-5-(2-propenyl)-5H-dibenzo [a,d]cyclohepten-5-yl]-1-methyl-1,2,5,6-tetrahydropyridine (0.33 g, 1.0 mmol) in 50 mL of absolute ethanol, and added 0.15 g of 10% palladium on carbon catalyst. Hydrogenated on a Paar shaker at 60 psi of hydrogen pressure for 24 hours. Filtered catalyst, and evaporated filtrate. Crystallized product from dichloromethane-ether to give 26 mg (8% yield) of 4-[10,11-dihydro-5-propyl-5H-dibenzo[a,d]cyclohepten-5-yl]-1-methylpiperidine as a tan solid.

mp=180°–185° C.

mass spectrum: (Cl, CH₄) m/e 334 (M+1)

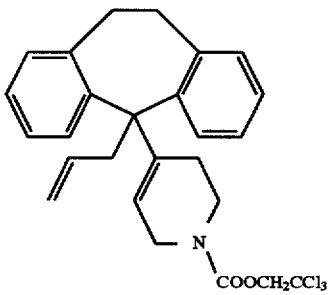

To synthesize an intermediate (step 4 of Scheme 1):

Dissolved 4-[10,11-dihydro-5-(2-propenyl)-5H-dibenzo [a,d]cyclohepten-5-yl]-1-methyl-1,2,5,6-tetrahydropyridine (3.3 g, 10.0 mmol) in 50 mL of benzene, and added 2,2,2-trichloroethylchloroformate (3.0 mL, 4.6 g, 21.8 mmol). Refluxed for 20 hours under a nitrogen atmosphere. Cooled to room temperature, and added water. Extracted with ether. Dried combined organic extracts with MgSO₄, filtered, and evaporated. Purified crude product by flash chromatography on silica gel eluting with dichloromethane. Combined appropriate fractions, and evaporated to give 3.7 g (75% yield) of 2,2,2-trichloroethyl 4-[10,11-dihydro-5-(2-propenyl)-5H-dibenzo[a,d]cyclohepten-5-yl]-1,2,5,6-tetrahydro-pyridinecarboxylate as an oil.

mass spectrum: (FAB) m/e 490 (M+1)

The following compounds were obtained according to a similar manner:

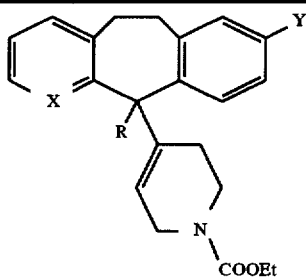

| X | Y | R | mp | Mass Spectrum |
|---|---|---|---|---|
| C | H | allyl | oil | (Cl, CH₄) m/e 388 (M + 1) |
| N | Cl | SMe | oil | (EI) m/e 428 (M+) |
| N | Cl | SEt | foam | (EI) m/e 442 (M+) |
| N | Cl | SPh | foam | (FAB) m/e 491 (M + 1) |

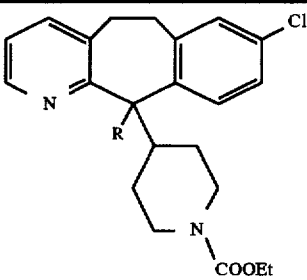

| R | mp | Mass Spectrum |
|---|---|---|
| SPh | foam | (FAB) m/e 493 (M + 1) |
| allyl | 159–161° C. | (FAB) m/e 425 (M + 1) |
| benzyl | | (FAB) m/e 476 (M + 1) |

For Compound IE:

Dissolved 2,2,2-trichloroethyl 4-[10,11-dihydro-5-(2-propenyl)-5H-dibenzo[a,d]cyclohepten-5-yl]-1,2,5,6-tetrahydropyridinecarboxylate (2.6 g, 5.3 mmol) in 70 mL of glacial acetic acid, and added zinc dust (1.49 g, 22.8 mmol) portionwise. Heated at 75° C. under a nitrogen atmosphere for 3 hours. Filtered, and evaporated filtrate. Added 10% HCl, and washed with ether. Made aqueous solution basic with concentrated NH₄OH, and extracted with dichloromethane. Dried combined organic extracts with MgSO₄, filtered, and evaporated to give 1.12 g (67% yield) of 4-[10,11-dihydro-5-(2-propenyl)-5H-dibenzo[a,d] cyclohepten-5-yl]-1,2,5,6-tetrahydro(1H)-pyridine as an oil. Dissolved free base in ether, and acidified with 19 weight % HCl-ethanol. Added additional ether to precipitate hydrochloride salt.

mp=130°–140° C.

mass spectrum: (FAB) m/e 316 (M+1)

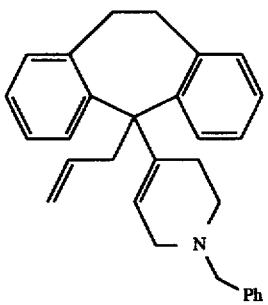

IN

For Compound IN:

Dissolved 4-[10,11-dihydro-5-(2-propenyl)-5H-dibenzo[a,d]cyclohepten-5-yl]-1,2,5,6-tetrahydro(1H)-pyridine (0.85 g, 2.7 mmol) in 20 mL of absolute ethanol. Added sodium bicarbonate (0.28 g, 3.3 mmol) and benzyl chloride (0.34 g, 2.7 mmol). Stirred at room temperature for 48 hours. Filtered, and evaporated filtrate. Purified crude product by flash chromatography on silica gel eluting with ethyl acetate. Combined appropriate fractions, and evaporated to give 0.60 g (55% yield) of 4-[10,11-dihydro-5-(2-propenyl)-5H-dibenzo[a,d]cyclohepten-5-yl]-1-(phenylmethyl)-1,2,5,6-tetrahydro-1H-pyridine as an oil. Dissolved free base in ethyl acetate, and added one equivalent of maleic acid dissolved in ethyl acetate. Added ether, and cooled to 0° C. to precipitate maleate salt. Recrystallized from ethyl acetate.

mp=112°–115° C.

mass spectrum: (FAB) m/e 406 (M+1)

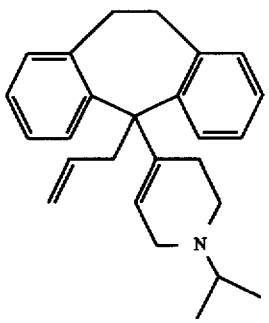

IP

For Compound IP:

Dissolved 4-[10,11-dihydro-5-(2-propenyl)-5H-dibenzo[a,d]cyclohepten-5-yl]-1,2,5,6-tetrahydro(1H)-pyridine (0.68 g, 2.15 mmol) in 6 mL of methanol. Added acetone (4.57 g, 81.7 mmol), aluminum foil (0.36 g, 13 mmol), and mercuric chloride catalyst (0.015 g, 0.06 mmol). Stirred at room temperature for 48 hours. Filtered through celite, and evaporated filtrate. Purified crude product by flash chromatography on silica gel eluting with ethyl acetate. Combined appropriate fractions, and evaporated to give 0.20 g (26% yield) of as an oil. Dissolved free base in ethyl acetate, and added one equivalent of maleic acid dissolved in ethyl acetate. Added ether, and let stand to precipitate maleate salt.

mp=135°–137° C.

mass spectrum: (FAB) m/e 358 (M+1)

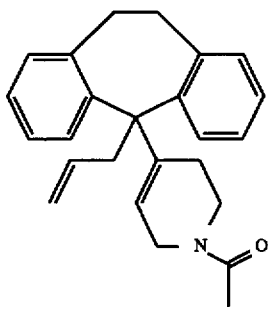

IG

For Compound IG:

Dissolved 4-[10,11-dihydro-5-(2-propenyl)-5H-dibenzo[a,d]cyclohepten-5-yl]-1,2,5,6-tetrahydro(1H)-pyridine (0.55 g, 1.74 mmol) in 15 mL of dichloromethane. Added 2 mL of acetic anhydride, and refluxed for 1 hour. Cooled to room temperature, and evaporated. Added water, and extracted with ether. Dried combined organic extracts with MgSO$_4$, filtered, and evaporated. Purified crude product by flash chromatography on silica gel eluting with 1:1 ethyl acetate:hexane. Combined appropriate fractions, and evaporated to give 0.080 g (13% yield) of 1-acetyl-4-[10,11-dihydro-5-(2-propenyl)-5H-dibenzo[a,d]cyclohepten-5-yl]-1,2,5,6-tetrahydro-1H-pyridine as a white glassy solid.

mp=98°–105° C.

mass spectrum: (CI, CH$_4$) m/e 358 (M+1)

The following compounds were obtained according to a similar manner:

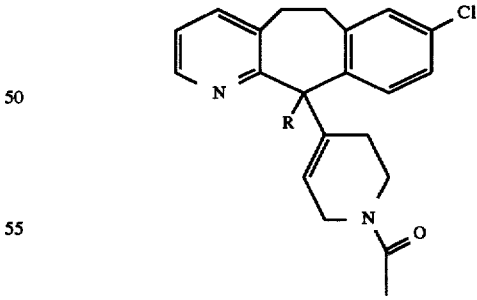

| R | mp | Mass Spectrum |
|---|---|---|
| Me | 90–100° C. | (EI) m/e 336 (M+) |
| allyl | oil | (FAB) m/e 393 (M + 1) |
| SMe | foam | (EI) m/e 398 (M+) |
| SEt | foam | (EI) m/e 412 (M+) |
| SPh | foam | (CI, CH$_4$) m/e 461 (M + 1) |
| SCH$_2$Ph | 160–165° C. | (FAB) 443 (M + 1) |
| CH$_2$CH$_2$COOEt | foam | (FAB) m/e 453 (M + 1) |

-continued

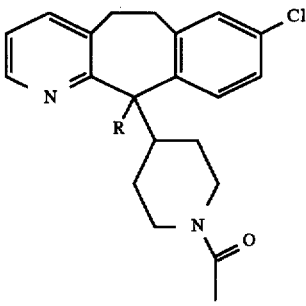

| R | mp | Mass Spectrum |
|---|---|---|
| methyl | oil | (FAB) m/e 369 (M + 1) |
| ethyl | 168–179° C. | (EI) m/e 382 (M+) |
| allyl | foam | (Cl, CH$_4$) m/e 395 (M + 1) |
| benzyl | wax | (FAB) m/e 445 (M + 1) |
| SPh | foam | (Cl, CH$_4$) m/e 463 (M + 1) |

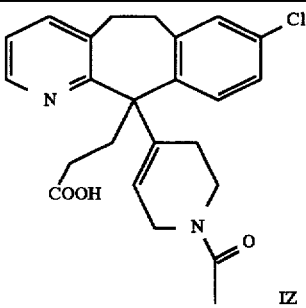

IZ

FOR COMPOUND IZ:

Dissolved ethyl 3-[8-chloro-11-(1-acetyl-1,2,5,6-tetrahydro-4-pyridinyl)-5,6-dihydro-11H-benzo[5,6]cyclopenta[1,2-b]pyridin-11-yl]-propionic acid (1.6 g, 3.53 mmol) in 30 mL of ethanol, and added potassium hydroxide (0.34 g of 85%, 5.2 mmol). Stirred at room temperature for 16 hours. Evaporated, and added ethyl acetate. Washed organic solution three times with water, dried with MgSO$_4$, filtered, and evaporated to give 0.75 g (46% yield) of recovered starting material. Acidified combined aqueous extracts with concentrated HCl to pH=4, and extracted with dichloromethane. Dried combined organic extracts with MgSO$_4$, filtered, and evaporated to give 0.30 g (20% yield) of 3-[8-chloro-11-(1-acetyl-1,2,5,6-tetrahydro-4-pyridinyl)-5,6-dihydro-11H-benzo[5,6]cyclopenta[1,2-b]pyridin-11-yl]-propionic acid as a foam.

mass spectrum: (FAB) m/e 425 (M+1)

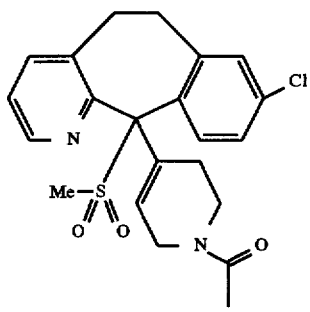

IAA

FOR COMPOUND IAA:

Dissolved 1-acetyl-4-(8-chloro-5,6-dihydro-11-methylthio-511-benzo[5,6]cyclohepta[1,2-b]pyridin-11-yl)-1,2,5,6-tetrahydropyridine (0.40 g, 1.0 mmol) in 10 mL of dichloromethane. Cooled to 0° C. under a nitrogen atmosphere. Added m-chloroperoxybenzoic acid (0.7 g of 80–85%, 3.3 mmol). Stirred at 0° C. for 15 mins and at room temperature for 30 mins. Added saturated NaHCO$_3$, and stirred at room temperature for 30 mins. Separated layers, and extracted with dichloromethane. Dried combined organic extracts, filtered, and evaporated. Purified crude product by flash chromatography on silica gel eluting with 1% Et$_3$N-EtOAc then 3% Et$_3$N-EtOAc. Combined appropriate fractions, and evaporated to give 0.12 g (28% yield) of 1-acetyl-4-(8-chloro-5,6-dihydro-11-methylsulfonyl-11H-benzo[5,6]cyclohepta[1,2-b]pyridin-11-yl)-1,2,5,6-tetrahydropyridine as a white solid.

mp=163°–165° C.

mass spectrum:(FAB) m/e 415 (M+1)

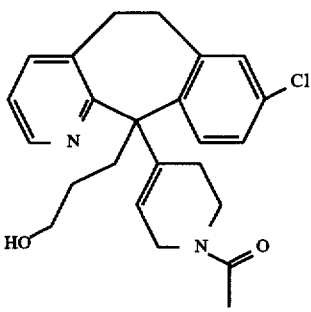

IBB

FOR COMPOUND IBB:

Dissolved 1-acetyl-4-(8-chloro-5, 6-dihydro-11-(2-propenyl)-11H-benzo[5,6]-cyclohepta[1,2-b]pyridin-11-yl)-1,2,5,6-tetrahydropyridine(1.0 g, 2.5 mmol) in 50 mL of dry THF, and cooled to 0° C. under a nitrogen atmosphere. Added 9-borabicyclo-[3.3.1]nonane (12.5 mL of 0.5M, 6.25 mmol) via syringe. Warmed slowly room temperature, and stirred for 4 hours. Added 25 weight % NaOH (7.8 mL, 20 mmol) and 30 weight % hydrogen peroxide (4.9 mL, 17.5 mmol), and stirred at room temperature for 16 hours. Added dichloromethane, and washed with saturated NaHSO$_3$, water, and then saturated NaCl. Dried organic solution with MgSO$_4$, filtered, and evaporated. Purified crude product by flash chromatography on silica gel eluting with 10% MeOH-EtOAc. Combined appropriate fractions, and evaporated to give 0.16 g (16% yield) of 1-acetyl-4-(8-chloro-5,6-dihydro-11-(3-hydroxypropyl)-11H-benzo[5,6]cyclohepta[1,2-b]pyridin-11-yl)-1,2,5,6-tetrahydropyridine as an oil.

elemental: C=69.96%, H=6.79%, N=6.45%

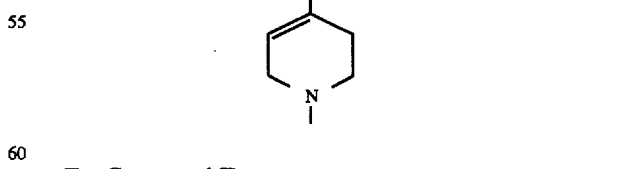

IL

For Compound IL:

Dissolved 4-(10,11-dihydro-5H-dibenzo[a,d]cyclohepten-5-ylidene)-1-methylpiperidine (12 g, 0.042 mol) in 250 mL of dry THF. Cooled to -78° C. under a nitrogen atmosphere. Added n-butyl lithium (18 mL of 2.5M in hexane) dropwise via addition funnel. Maintain temperature at 0° C. for 1 hour then recooled to −78° C. Added 21 mL of dry methanol, and let warm to room temperature. Added saturated NH₄Cl, and extracted with THF. Dried combined organic extracts with MgSO₄, filtered, and evaporated to give 11.3 g (94% yield) of 4-(10,11-dihydro-5H-dibenzo[a,d]cyclohepten-5-yl)-1-methyl-1,2,5,6-tetrahydropyridine as a white solid.

mp=96°-98° C.

mass spectrum: (FAB) m/e 290 (M+1)

The following compound was obtained according to a similar manner:

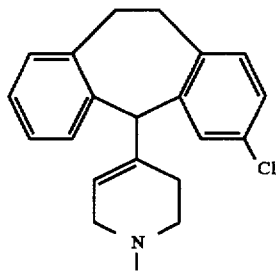

ICC mp = 111-112° C.
MS(Cl, CH₄) m/e 324 (M + 1)

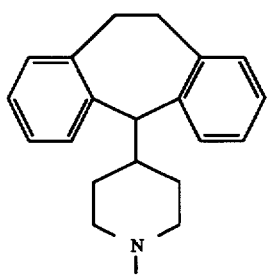

K

For Compound K:

Dissolved 4-(10,11-dihydro-5H-dibenzo[a,d]cyclohepten-5-yl)-1-methyl-1,2,5,6-tetrahydropyridine (10.5 g, 0.036 mol) in 100 mL of glacial acetic acid and 60 mL of absolute ethanol. Added platinum oxide catalyst (1.5 g). Shake on Paar shaker at 60 psi of hydrogen pressure for 24 hours. Filtered, and washed catalyst with ethanol. Evaporated filtrate. Purified crude product by flash chromatography on silica gel eluting with 17% MeOH-EtOAc. Combined appropriate fractions, and evaporated to give 5.7 g (54% yield) of as a white solid.

mp=88°-89° C.

mass spectrum: (FAB) m/e 292 (M+1)

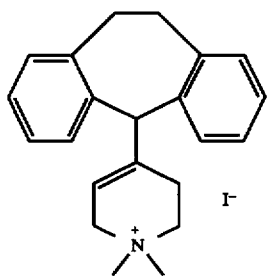

IY

For Compound IY:

Dissolved 4-(10,11-dihydro-5H-dibenzo[a,d]cyclohepten-5-yl)-1-methyl-1,2,5,6-tetrahydropyridine (0.80 g, 2.8 mmol) in 25 mL of methanol, and added 1 mL of iodomethane. Refluxed for 1 hour. Cooled to room temperature, and evaporated. Triturated solid with 1:2 acetonitrile:ether to give 1.1 g (92% yield) of 4-(10,11-dihydro-5H-dibenzo[a,d]cyclohepten-5-yl)-1,1-dimethyl-1,2,5,6-tetrahydropyridinium iodide as a cream solid.

mp>300° C.

mass spectrum: (Cl, CH₄) m/e 290 (M+1 for free base)

The following compound was obtained according to a similar manner:

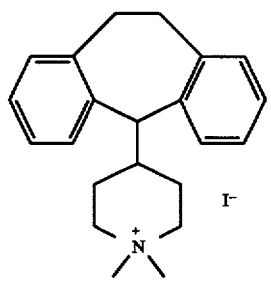

IU mp > 300° C.
Ms (FAB) m/e 306 (M-iodide)

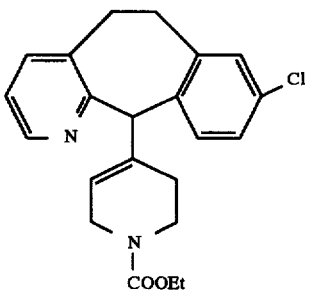

IDD

FOR COMPOUND IDD:

Dissolved 4-(8-chloro-5,6-dihydro-11H-benzo[5,6]cyclohepta[1,2-b]pyridin-11-yl)-N-methyl-1,2,5,6-tetrahydropyridine (1.24 g, 3.82 mmol) in 100 mL of dry toluene, and added ethyl chloroformate (0.91 mL, 9.54 mmol) via syringe. Heated at 80° C. for 46 hours under a nitrogen atmosphere. Cooled to room temperature, and added 1N NH₄OH. Extracted with ether. Purified crude product by flash chromatography on silica gel eluting with 10% EtOAc-CH₂Cl₂. Combined appropriate fractions, and evaporated to give 0.39 g (27% yield) of ethyl 4-(8-chloro-5,6-dihydro-11H-benzo[5,6]cyclohepta[1,2-b]pyridin-11-yl)-1,2,5,6-tetrahydropyridinecarboxylate as an oil. mass spectrum: (Cl, CH₄) m/e 383 (M+1)

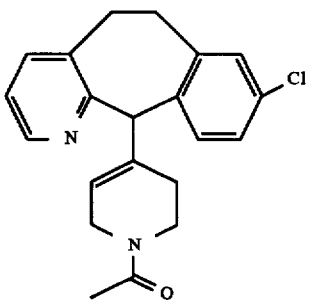

IEE

FOR COMPOUND IEE:

Dissolved ethyl 4-(8-chloro-5,6-dihydro-11H-benzo[5,6]cyclohepta[1,2-b]pyridin-11-yl)-1,2,5,6-tetrahydropyridinecarboxylate (0.35 g, 0.91 mmol) in 7 mL of ethanol and 3 mL of water. Added potassium hydroxide (0.40 g, 7.1 mmol), and refluxed for 18 hours. Added ice and concentrated HCl. Washed with ethyl acetate. Extracted ethyl acetate washings with water. Combined all aqueous solutions, and made basic with concentrated NH₄OH. Extracted basic aqueous solution with dichloromethane. Dried combined dichloromethane extracts with MgSO₄, filtered, and evaporated to give 0.23 g of an oil. Dissolved oil in 10 mL of dichloromethane, and added acetic anhydride (0.5 g). Refluxed for 2 hours. Added ice, and made basic with concentrated NH₄OH. Extracted with dichloromethane. Dried combined organic extracts with MgSO₄, filtered, and evaporated. Purified crude product by flash chromatography on silica gel eluting with 2% MeOH-EtOAc. Combined appropriate fractions, and evaporated to give 130 mg (40% yield) of 1-acetyl-4-(8-chloro-5,6-dihydro-11H-benzo[5,6]cyclohepta[1,2-b]pyridin-11-yl)-1,2,5,6-tetrahydropyridine as a foam.

mass spectrum: (Cl, CH₄) m/e 353 (M+1)

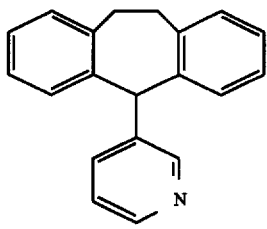

For Compound IW:

Heated 10,11-dihydro-5-(3-pyridinyl)-5H-dibenzo[a,d]cyclohepten-5-ol (0.47 g, 1.6 mmol) in 1.5 mL of glacial acetic acid, 0.5 mL of concentrated HCl, and 2.5 mL of 57% hydriodic acid at reflux for 3 hours. Cooled to room temperature, and added 10 mL of acetone, 15 mL of 7% sodium sulfite, and 8 mL of 40% NaOH in sequence. Filtered the precipitate, and recrystallized from hexane to give 0.28 (63% yield) of 3-(10,11-dihydro-5H-dibenzo[a,d]cyclohepten-5-yl)-pyridine as a white solid.

mp=119°–120° C.

mass spectrum: (Cl, CH₄) m/e 272 (M+1)

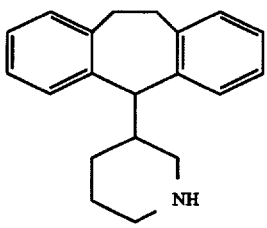

For Compound ID:

Dissolved 3-(10,11-dihydro-5H-dibenzo[a,d]cyclohepten-5-yl)-pyridine (0.95 g, 3.5 mmol) in 50 mL of glacial acetic acid. Added platinum oxide catalyst (0.2 g), and shook on Paar shaker at 59 psi of hydrogen pressure for 24 hours. Filtered, and evaporated filtrate. Crystallized product from ether to give 1.14 g (100% yield) of 3-(10,11-dihydro-5H-dibenzo[a,d]cyclohepten-5-yl)-piperidine acetic acid as a white solid.

mp=110°–111° C.

mass spectrum: (Cl, CH₄) m/e 278 (M+1 for free base)

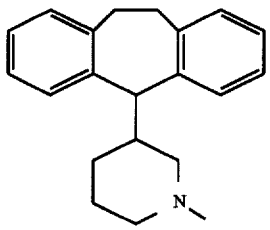

For Compound IR:

Dissolved 3-(10,11-dihydro-5H-dibenzo[a,d]cyclohepten-5-yl)-piperidine (0.75 g, 2.7 mmol) in 1.1 mL of formic acid and 1.5 mL of 37% aqueous formaldehyde. Heated in a 90°–95° C. oil bath for 20 hours. Cooled to room temperature, and made basic with 5% NaOH. Extracted with ether. Dried combined organic extracts with MgSO₄, filtered, and evaporated. Crystallized product from hexane to give 0.60 g (76% yield) of 3-(10,11-dihydro-5H-dibenzo[a,d]cyclohepten-5-yl)-1-methyl-piperidine as white solid. Dissolved the free base in ether, and added 19 weight % HCl-EtOH to precipitate the hydrochloride salt.

mp=311°–312° C.

mass spectrum: (Cl, CH₄) m/e 292 (M+1 for free base)

As mentioned above, the compounds of formula I exhibit good anti-TNF-α activity. The compounds of the invention are, therefore, useful when TNF-α activity is a factor in a given disease or disorder such as in the case of septic shock and various allergic diseases and inflammatory conditions.

The anti-TNF-α properties of the compounds of the present invention may be demonstrated by use of a standard in vitro pharmacological testing procedure as described below. This test procedure is a standard test used to determine anti-TNF-α activity and to evaluate the usefulness of said compounds for counteracting the biological effects of TNF-α.

In Vitro Study: Inhibition of LPS-Induced TNF-α Production From the Murine Cell Line WEHI-265

1) Cells (obtained from cell cultures containing ≦10⁶ cells/ml) are suspended at 0.2×10⁶ cells/ml in complete medium (RPMI1640, with 10% FCS, 10⁻⁵ M 2-ME, 2 mM glutamine and 10 mM HEPES buffer) and plated in CoStar 24 well plates (1.0 ml/well).

2) Compounds are dissolved in the appropriate vehicle at 400 times the concentration to be tested, and 5 μl of compound is added to the wells.

3) LPS (from E. coli 0111:B4) is diluted to 6 μg/ml and 1.0 ml is added to wells.

4) Plates are incubated 20–24 hours in 37° C. CO₂ incubator.

5) Supernatant fluids are collected and analyzed for TNF content as described in J. Immunol., 142:3884.

The Results of this procedure are shown in TABLE 1 below.

TABLE 1

| COMPOUND | % INHIBITION AT 10 µM |
|---|---|
| IA | 80 |
| IB | 70 |
| IC | 20 |
| ID | 51 |
| IE | 61 |
| IF | 28 |
| IG | 27 |
| IH | 6 |
| IJ | 55 |
| IK | 61 |
| IL | 23 |
| IM | 8 |
| IN | 25 |
| IP | 62 |
| IQ | 62 |
| IR | 60 |
| IS | 61 |
| IT | 9 |
| IX | 38 |
| IY | 12 |
| K | 17 |

In addition to the in vitro test described above, the following in vivo test was also performed on several of the compounds of the present invention. Although the individual reported values may be subject to a wide margin of error, collectively the in vivo data demonstrates that the compounds of the invention are inhibitors of TNF-α in a mammalian species.

2. In Vivo Study: Inhibition of LPS-Induced Serum TNF

1) Mice (C57Bl/6J males, 6–8 weeks of age) are dosed with the indicated compound (dissolved in CMC suspension vehicle; compounds are given orally or i.p. one hour before LPS challenge).

2) Mice are challenged with LPS (from E. coli 0111:B4; 50 µg i.p.).

3) Mice are bled 90 min after LPS challenge.

4) Sera are analyzed for TNF content by ELISA as described in J. Immunol. 142:3884.

Results are shown in TABLE 2 below.

TABLE 2

| COMPOUND | % INHIBITION AT 25 MG/KG |
|---|---|
| IB | 80 |
| IF | 50 |
| IH | 8 |
| IK | 45 |
| IL | 58 |
| IM | 27 |
| IN | 42 |
| IP | 28 |
| IQ | 28 |
| IS | 26 |
| IT | 3 |
| IX | 56 |
| K | 82 |

The effect of the compounds of the present invention against septic shock may be demonstrated by use of a standard pharmacological testing procedure as described below. This test procedure is a standard test used to determine activity against septic shock.

3. In Vivo Study: Inhibition of LPS/Galactosamine-Induced Lethality

Mice (C57Bl/6J males, 6–8 weeks of age) are dosed with the indicated compound (dissolved in CMC suspension vehicle; compounds are given orally or i.p. one hour before challenge with LPS and d-galactosamine).

Mice are challenged i.p. with a mixture of LPS (from E. coli 0111:B4; 100 ng) and d-galactosamine (8 mg).

Survival is determined 24 hours after challenge. See procedure
published in J. Exp. Med. 165:657 (1987)
Results are shown in TABLE 3 below.

TABLE 3

| COMPOUND | # DEAD/TOTAL AT 25 MG/KG |
|---|---|
| IB | 0/8 |
| IC | 4/8 |
| IE | 7/8 |
| IF | 5/8 |
| IH | 4/9 |
| IK | 5/9 |
| IL | 1/9 |
| IM | 2/11 |
| IN | 10/10 |
| IP | 6/10 |
| IQ | 4/10 |
| IX | 9/9 |
| K | 0/10 |

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective mount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to achieve relief of the symptoms.

DOSAGE FORMS

The following are examples of pharmaceutical dosage forms which contain a compound of the invention. As used therein, the term "active compound" is used to designate the compound

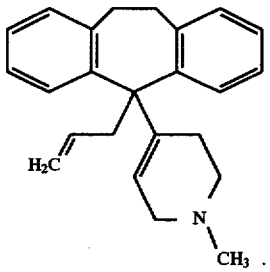
(IB)

The scope of the invention in its pharmaceutical composition aspect is not to be limited by the examples provided, since any other compound of Formula I can be substituted into the pharmaceutical composition examples.

Pharmaceutical Dosage Form Examples

| EXAMPLE A Tablets | | | |
|---|---|---|---|
| No. | Ingredients | mg/tablet | mg/tablet |
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

| EXAMPLE B Capsules | | | |
|---|---|---|---|
| No. | Ingredient | mg/capsule | mg/capsule |
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
| | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A method of inhibiting tumor necrosis factor-α comprising administering to a mammal in need of such inhibition an effective anti-tumor necrosis factor amount of a compound of the Formula I:

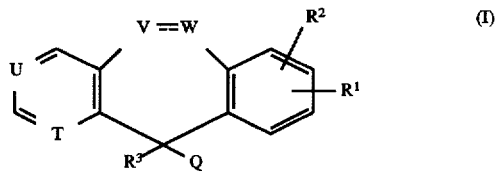

or a pharmaceutically acceptable salt or solvate thereof, wherein:

one of T and U represents N and the other represents =CH—; or each of T and U represents =CH—;

the ------ line represents an optional double bond; when ------ a double bond, each of V and W represents =CH—; when ------ represents a single bond, one of V and W represents oxygen and the other represents —CH$_2$—; or each of V and W represents —CH$_2$—;

R$^1$ and R$^2$ are each independently selected from the group consisting of H and halogen;

R$^3$ is; alkyl; alkenyl; alkynyl; aryl; alkaryl; aralkyl; cycloalkyl; alkoxy; (CH$_2$)$_n$OR$^{10}$; (CH$_2$)$_n$COOR$^{10}$, wherein n is 1 to 3 and R$^{10}$ is or lower alkyl; or S(O)$_e$R$^{11}$, wherein e is 0 or 2 and R$^{11}$ is alkyl or aryl;

Q represents

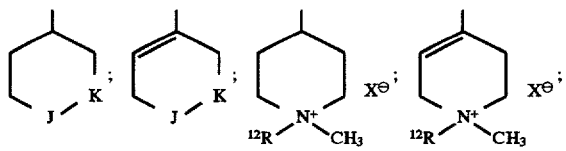

-continued

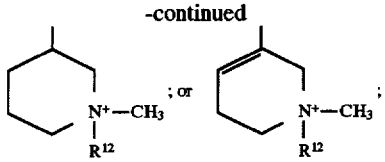

wherein one of J and K represents

and the other represents —CH$_2$—, with the proviso that when R$^3$ is H, Q is limited to either:

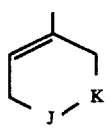 or 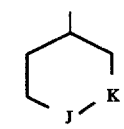 wherein J is —CH$_2$—;

R$^{12}$ is lower alkyl;

R$^{16}$ is H; lower alkyl; aryl; aralkyl; alkaryl; COR$^{17}$ or C(O)OR$^{18}$, wherein R$^{17}$ is H or lower alkyl or aryl, R$^{18}$ is lower alkyl or aryl; and X represents halogen.

2. A method according to claim 1, wherein R$^3$ is alkyl.
3. A method according to claim 2, wherein R$^3$ is propyl.
4. A method according to claim 3, wherein Q is:

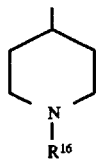

or

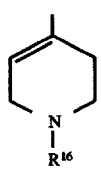

wherein R$^{16}$ is H, lower alkyl, aryl, aralkyl or alkaryl.

5. A method according to claim 4, wherein the compound of Formula I has the following structure:

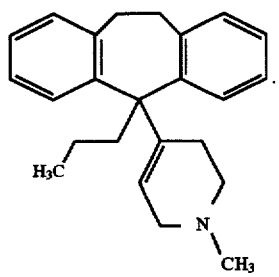

(IF)

6. A method according to claim 4, wherein the compound of Formula I has the following structure:

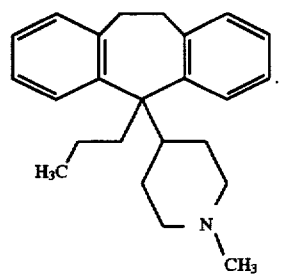

(IJ)

7. A method according to claim 1, wherein R$^3$ is alkenyl.
8. A method according to claim 7, wherein R$^3$ is allyl.
9. A method according to claim 8, wherein Q is:

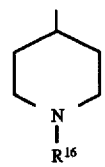

or

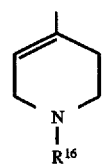

wherein R$^{16}$ is H, lower alkyl, aryl, aralkyl or alkaryl.

10. A method according to claim 9, wherein Q is:

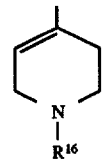

wherein R$^{16}$ is H, lower alkyl, aryl, aralkyl or alkaryl.

11. A method according to claim 10, wherein the compound of Formula I has the following structure:

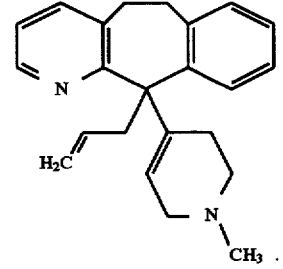

(IX)

12. A method according to claim 10, wherein the compound of Formula I has the following structure:

13. A method according to claim 10, wherein the compound of Formula I has the following structure:

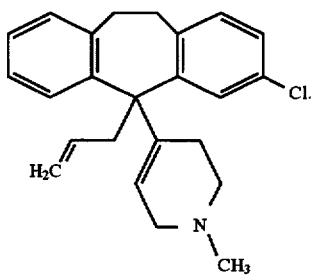
(IA)

14. A method according to claim 1, wherein Q represents:

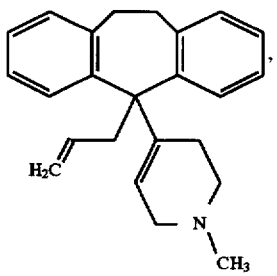

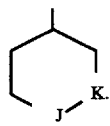
K.

15. A method according to claim 1, wherein each of T and U represents =CH—.

16. A method according to claim 1, wherein R³ is H and Q is:

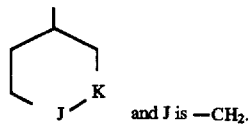
and J is —CH₂.

17. A method according to claim 16, wherein the compound of Formula I has the following structure:

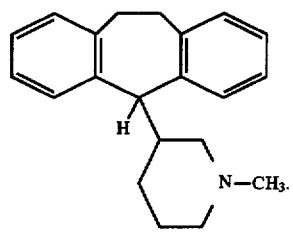
(IR)

18. A method of inhibiting tumor necrosis factor-α comprising administering to a mammal in need of such inhibition an effective anti-tumor necrosis factor amount of a pharmaceutical composition comprising an effective amount of a compound of the following structure IB in combination with a pharmaceutically acceptable carrier:

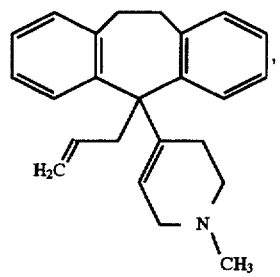
(IB)

19. A method of inhibiting tumor necrosis factor-α comprising administering to a mammal in need of such inhibition an effective anti-tumor necrosis factor amount of a compound having the following structure K:

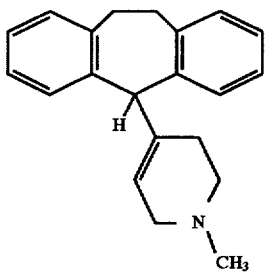
(K)

* * * * *